US010486146B2

(12) United States Patent
Bae et al.

(10) Patent No.: US 10,486,146 B2
(45) Date of Patent: Nov. 26, 2019

(54) ZEOLITE-BASED COMPOUND HAVING HIGH CRYSTALLINITY, METHOD FOR PRODUCING THE SAME, AND METHOD FOR PRODUCING METHYL ACETATE USING THE SAME

(71) Applicant: Research & Business Foundation Sungkyunkwan University, Suwon-si (KR)

(72) Inventors: Jong Wook Bae, Suwon-si (KR); Ji Hyeon Kim, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 15/966,302

(22) Filed: Apr. 30, 2018

(65) Prior Publication Data

US 2018/0311654 A1   Nov. 1, 2018

(30) Foreign Application Priority Data

Apr. 28, 2017   (KR) ........................ 10-2017-0055489

(51) Int. Cl.
| | |
|---|---|
| *B01J 29/06* | (2006.01) |
| *B01J 29/80* | (2006.01) |
| *B01J 29/65* | (2006.01) |
| *B01J 29/18* | (2006.01) |
| *B01J 29/40* | (2006.01) |
| *B01J 29/08* | (2006.01) |
| *B01J 35/00* | (2006.01) |
| *B01J 37/00* | (2006.01) |
| *B01J 37/10* | (2006.01) |
| *B01J 37/08* | (2006.01) |
| *B01J 37/30* | (2006.01) |
| *C07C 67/37* | (2006.01) |
| *B01J 37/02* | (2006.01) |
| *C07C 67/36* | (2006.01) |

(52) U.S. Cl.
CPC ............ *B01J 29/80* (2013.01); *B01J 29/084* (2013.01); *B01J 29/18* (2013.01); *B01J 29/40* (2013.01); *B01J 29/65* (2013.01); *B01J 35/0006* (2013.01); *B01J 37/0018* (2013.01); *B01J 37/0215* (2013.01); *B01J 37/0221* (2013.01); *B01J 37/0246* (2013.01); *B01J 37/08* (2013.01); *B01J 37/10* (2013.01); *B01J 37/30* (2013.01); *C07C 67/36* (2013.01); *C07C 67/37* (2013.01); *B01J 2229/183* (2013.01); *B01J 2229/60* (2013.01); *B01J 2229/62* (2013.01)

(58) Field of Classification Search
CPC . B01J 29/084; B01J 29/18; B01J 29/40; B01J 29/65; B01J 29/80; B01J 35/0006; B01J 37/0246; B01J 37/0221; B01J 37/0215; B01J 37/08; B01J 37/10; B01J 37/30; B01J 2229/60; B01J 2229/62; C07C 67/36; C07C 67/37; C07C 69/14
USPC ................ 502/4, 60, 64, 69, 71, 77, 78, 79; 560/232, 240, 129
See application file for complete search history.

(56) References Cited

U.S. PATENT DOCUMENTS

| | | | | |
|---|---|---|---|---|
| 5,972,202 | A * | 10/1999 | Benham | C10G 45/16 208/107 |
| 6,812,181 | B2 * | 11/2004 | van der Berge | B01J 29/80 502/61 |
| 7,314,964 | B2 * | 1/2008 | Abrevaya | C07C 4/06 585/651 |
| 9,889,438 | B2 * | 2/2018 | Yoon | C01B 37/02 |
| 2014/0256538 | A1 * | 9/2014 | Yoon | C01B 37/02 502/67 |

FOREIGN PATENT DOCUMENTS

KR   10-2013-0017165 A   2/2013

OTHER PUBLICATIONS

Ahedi et al. (Synthesis of Ferrierite-Type Zeolite in the Presence of a Catalytic Amount of Pyrrolidine and Sodium Bis(2-ethyhlhexyl) Sulfosuccinate), Journal of Colloid and Interface Science 236, 47-51, Published 2001) (Year: 2001).*
Zhou et al.(Promotion effect of Fe in mordenite zeolite on carbonylation of dimethyl ether to methyl acetate, Catal. Sci. Technol., , 5, 1961-1968, Published 2015) p. 1961. (Year: 2015).*
Bouizi et al., "Factors Controlling the Formation of Core-Shell Zeolite-Zeolite Composites", Chem. Mater., 2006, 18, pp. 4959-4966.*

\* cited by examiner

*Primary Examiner* — Elizabeth D Wood
(74) *Attorney, Agent, or Firm* — NSIP Law

(57) ABSTRACT

The present disclosure provides a zeolite-based compound having a high crystallinity, a method for producing the zeolite-based compound, and a method for producing methyl acetate using the zeolite-based compound. The zeolite-based compound includes a zeolite-based core; and a surface-portion formed on at least a portion of a surface of the zeolite-based core and made of ferrierite.

12 Claims, 2 Drawing Sheets

[FIG. 1]
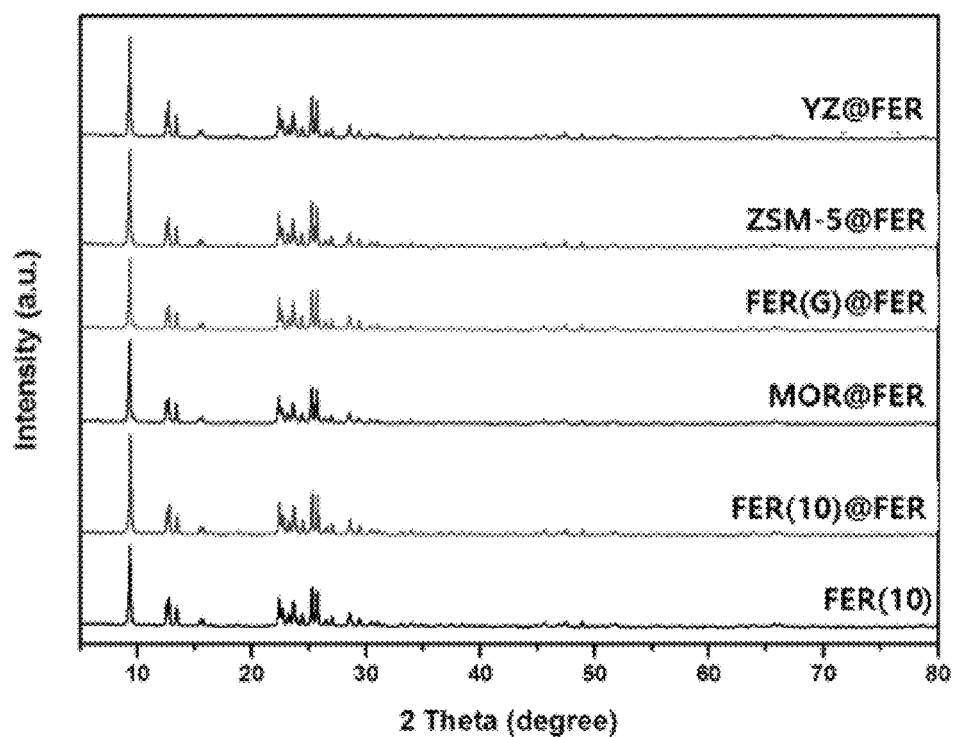
[FIG. 2]
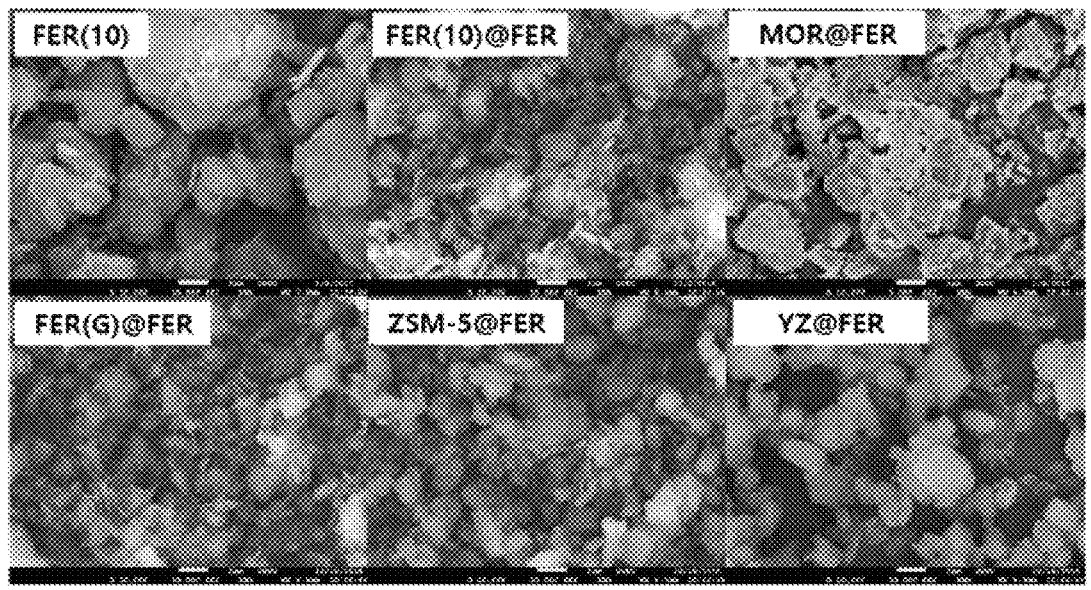

[FIG. 3]
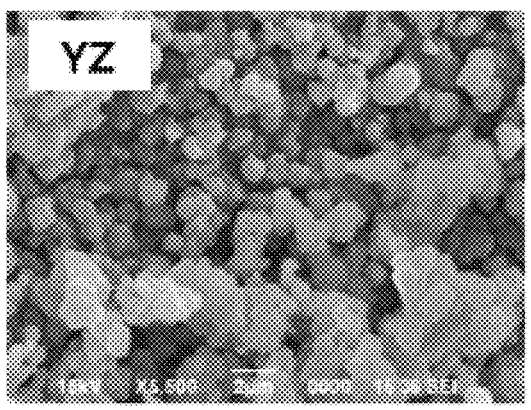
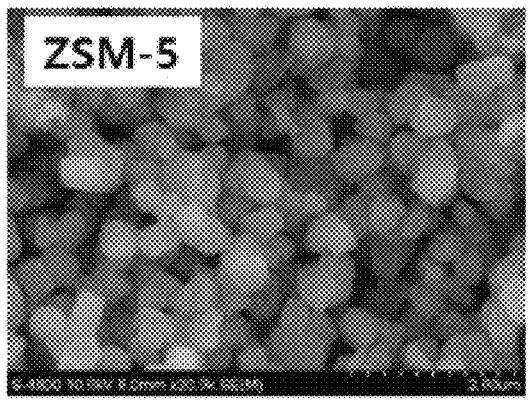
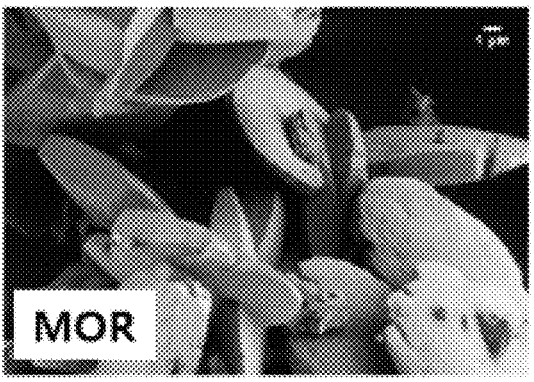

ZEOLITE-BASED COMPOUND HAVING HIGH CRYSTALLINITY, METHOD FOR PRODUCING THE SAME, AND METHOD FOR PRODUCING METHYL ACETATE USING THE SAME

FIELD

The present disclosure relates to a zeolite-based compound having a high crystallinity, a method for producing the zeolite-based compound, and a method for producing methyl acetate using the zeolite-based compound. More specifically, the present disclosure relates to the zeolite-based compound having the high crystallinity used as a catalyst for producing methyl acetate, the method for producing the zeolite-compound, and the method for producing methyl acetate using the zeolite-compound.

BACKGROUND

Continuous research is underway to solve depletion of petroleum resources and environmental pollution due to continuous industrialization. To this end, alternative energy, especially as eco-friendly energy has been developed. Ethanol as alternative energy resource under great interest has already been used as a solvent or base material in many fields, and its potential for use as an eco-friendly fuel mixed with gasoline has also been studied (Licht F. O. "*World Fuel Ethanol, analysis and outlook*"(2006)). There is a lot of research on a method for effectively producing not only ethanol but also other alcoholic compounds, especially methanol compounds.

Although a method using biomass is a main method for conventionally producing ethanol, it is costly to perform processes and a conversion rate is not so good. A catalyst process for directly synthesizing ethanol using syngas has been developed as an alternative to the method using biomass. However, also the direct ethanol synthesis process is inefficient because of a high selectivity of not only ethanol, as a main product, but also by-products. Further, the direct ethanol synthesis process has a disadvantage of high production cost because of using platinum or rhodium (*J. Catal.* 261 (2009), 9-16).

In a method for indirectly synthesizing ethanol, dimethyl ether (DME) is firstly produced by using syngas, and methyl acetate (MA) is secondly produced by a carbonylation of the dimethyl ether, and then the methyl acetate is hydrogenated to obtain ethanol finally. In this connection, it is efficient to use a zeolite catalyst for the carbonylation reaction of dimethyl ether for producing the methyl acetate. Especially, a crucial acetyl-group based intermediate generated in an 8-membered oxygen ring pore of a mordenite zeolite structure including the 8-membered oxygen ring pore and a 12-membered oxygen ring pore is activated in the carbonylation reaction of the dimethyl ether (*Angew. Chem.* 45 (2006) 1617-1620, *J. Catal.* 245 (2007)110-123, Korean Patent Registration No. 10-1391571).

However, the mordenite zeolite has a high selectivity at a low temperature, but it has a disadvantage in a conventional aspect in that the mordenite zeolite as the catalyst is inactivated rapidly. Further, from the conventional researches which have been conducted under mild conditions in which a molar ratio of carbon monoxide (CO) and dimethyl ether is 45:1 or above, a high conversion rate and the high selectivity are only natural results. However, there is a limit to solve problems of rapid inactivation of the catalyst due to coke generated in the actual reaction, and generation of hydrocarbon as a by-product.

SUMMARY

One object of the present disclosure is to provide a zeolite-based compound having a high crystallinity, which removes the conventionally known disadvantage of the zeolite which is known as a catalyst activated in the dimethyl ether carbonylation reaction.

Another object of the present disclosure is to provide a method for producing the zeolite-based compound having the high crystallinity as described above.

Still another object of the present disclosure is to provide a method for producing methyl acetate, in which a selectivity of the carbonylation reaction is improved by using the zeolite-based compound having the high crystallinity as described above.

In a first aspect of the present disclosure, there is provided a zeolite-based compound having a high crystallinity, the compound comprising: a zeolite-based core; and a surface-portion formed on at least a portion of a surface of the zeolite-based core, wherein the surface-portion is made of ferrierite.

In one embodiment, the ferrierite constituting the surface-portion is coated in a form of a plate on the surface of the zeolite-based core.

In one embodiment, the zeolite-based core includes at least one selected from a group consisting of H-ferrierite, mordenite, ZSM-5, and zeolite-Y.

In one embodiment, the zeolite-based core is made of a zeolite-based material including silicon and aluminum, wherein a molar ratio of the silicon and aluminum is in a range of 10:1 to 11:1.

In one embodiment, the ferrierite constituting the surface-portion has a molar ratio of silicon and aluminum in a range of 5:1 to 30:1

In one embodiment, the zeolite-based core and the surface-portion together form a core/shell structure.

In another aspect of the present disclosure, there is provided a method for producing a zeolite-based compound having a high crystallinity, the method comprising: synthesizing a seed made of a zeolite-based material; and synthesizing ferrierite on a surface of the seed using the seed as a structure-directing agent, wherein the seed defines a zeolite-based core of the zeolite-based compound, wherein the ferrierite is formed on at least a portion of the surface of the zeolite-based core, wherein the ferrierite defines a surface-portion of the zeolite-based compound.

In one embodiment, in synthesizing the ferrierite on the surface of the seed, the ferrierite formed on the surface of the seed compensates for crystal defects of the seed to enhance an overall crystallinity of the compound.

In one embodiment, synthesizing the ferrierite on the surface of the seed including: producing a silica structure using a basic silica solution and the seed as a structure-directing agent; hydrothermally synthesizing the silica structure with an alumina solution to form a hydrothermally synthesized product; firing the hydrothermally synthesized product to produce a basic-ferrierite; ion-exchanging the basic-ferrierite with an ammonium precursor to produce $NH_3$-ferrierite; and firing the $NH_3$-ferrierite to form the H-ferrierite on the surface of the seed.

In one embodiment, synthesizing the seed comprising: producing a silica structure using a basic silica solution and piperidine as a structure-directing agent; hydrothermally synthesizing the silica structure with an alumina solution to form a hydrothermally synthesized product; firing the hydrothermally synthesized product to produce a basic-ferrierite; ion-exchanging the basic-ferrierite with an ammonium precursor to produce $NH_3$-ferrierite; and firing the $NH_3$-ferrierite to form H-ferrierite as the seed.

In still another aspect of the present disclosure, there is provided a method for producing methyl acetate comprising: performing carbonylation of dimethyl ether using a catalyst, wherein the catalyst is a zeolite-based compound having a high crystallinity, wherein the compound includes a zeolite-based core, and a surface-portion formed on at least a portion of a surface of the zeolite-based core, wherein the surface-portion is made of ferrierite.

According to the zeolite-based compound with the high crystallinity, the method for producing the zeolite-based compound, and the method for producing methyl acetate using the zeolite-based compound as above-described, the zeolite-based compound with the high crystallinity has improved crystallinity by compensating for defects of the zeolite thereof using the seed. Thus, in a reaction using the zeolite-based compound as a catalyst, the selectivity of the selectivity of methyl acetate may be improved, and, at the same time, the selectivity of methanol, as a useful compound among the by-products may be also enhanced. In particular, the zeolite-based compound with the high crystallinity according to the present disclosure may enhance the selectivity of methyl acetate even under the condition when carbon monoxide content is not higher than in the conventional zeolite-based compound, that is, when the molar ratio of carbon monoxide(CO) and dimethyl ether is 10:1 or below. The improvement of the selectivity of methyl acetate may lead to improvement of the yield of the ethanol to be finally obtained. Performing the carbonylation of dimethyl ether using the zeolite-based compound according to the present disclosure may allow maintaining stable activation. Further, the zeolite-based compound may be easily synthesized by using the seed.

In addition, methanol, which is the by-product from the methyl acetate production, may be re-used as a base material for the dimethyl ether synthesis reaction used for producing methyl acetate. The methanol may further be utilized for the esterification reaction of acetic acid. Therefore, the recycling of methanol may enhance the final yield of ethanol or acetic acid in the overall esterification reaction.

BRIEF DESCRIPTION OF THE DRAWINGS

FIG. 1 shows a XRD analysis result of H-ferrierite and samples according to the present disclosure.

FIG. 2 shows SEM images of H-ferrierite and samples according to the present disclosure.

FIG. 3 shows SEM images of comparison samples.

DETAILED DESCRIPTIONS

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The zeolite-based compound having the high crystallinity according to the present disclosure includes a zeolite-based core, and a surface-portion formed on at least a portion of a surface of the zeolite-based core and made of ferrierite. For example, the zeolite-based compound according to the present disclosure may have a core/shell structure including the zeolite-based core and a shell-layer as the surface portion formed on the surface of the zeolite-based core.

The zeolite-based core acts as a seed of the zeolite-based compound according to the present disclosure, and the core may be composed of at least one zeolite-based material. Examples of the zeolite-based materials include, but is not limited thereto, ferrierite, mordenite, ZSM-5(Zeolite Socony Mobil-5 (framework type MFI from ZSM-5 (five)), and zeolite-Y, and the like.

In one embodiment, the zeolite-based core may be H-ferrierite. In this connection, a molar ratio of silicon and aluminum in the H-ferrierite may be from 10:1 to 11:1, and more preferably, 10.4:1. When the molar ratio of silicon and aluminum is within the above range, the selectivity of the methyl acetate may be enhanced and hydrocarbon as a by-product may be reduced using the zeolite-based compound having the above range of the molar ratio as the catalyst.

The ferrierite constituting the surface-portion may be H-ferrierite and may be directly synthesized on the surface of the seed in the process of producing the zeolite-based compound according to the present disclosure. In the resulting zeolite-based compound, the seed corresponds to the zeolite-based core, and the ferrierite synthesized on the surface of the zeolite-based core corresponds to the surface-portion.

The molar ratio of silicon and aluminum in the ferrierite constituting the surface-portion may be from 5:1 to 30:1. When the molar ratio of silicon-to-aluminum is within the above range, it is possible to achieve the reduction of hydrocarbon which is a by-product in the reaction using the zeolite-based compound as the catalyst.

The zeolite-based compound having the high crystallinity according to the present disclosure may be produced by first synthesizing the seed made of the zeolite-based material (step 1), and synthesizing the ferrierite using the seed as a structure-directing agent (step 2).

When synthesizing the seed (step 1), the zeolite-based material constituting the seed may be produced by a conventional manufacturing method.

In one embodiment, when the seed is H-ferrierite, the H-ferrierite may be produced as follows. A silica structure may be produced by using a basic silica solution and using piperidine as the structure-directing agent. Then, the silica structure may be hydrothermally synthesized with alumina solution and then may be subjected to cooling, washing, drying, and fired, thereby to form a basic-ferrierite. Then, $NH_3$-ferrierite may be produced by ion-exchanging the basic-ferrierite using ammonium precursor. Then, the $NH_3$-ferrierite may be fired to form the H-ferrierite.

When synthesizing the ferrierite (step 2), the prepared seed is used as the structure-directing agent to synthesize ferrierite on the surface of the seed.

In one embodiment, the process of synthesizing the H-ferrierite as the surface-portion includes producing the silica structure using the basic silica solution and the zeolite-based material as the structure-directing agent (seed); then, hydrothermally synthesizing the silica structure with alumina solution and then cooling, washing, drying, and firing the hydrothermally synthesized product between the silica structure with alumina solution to form a fired hydrothermally synthesized product; exchanging ions between the fired hydrothermally synthesized product and ammonium precursor to produce $NH_3$-ferrierite; then, firing the $NH_3$-ferrierite, form the H-ferrierite.

Since the two synthesis steps as described above are carried out, the portion of the zeolite-based core produced in the first synthesis step, which did not form a complete crystalline structure, is supplemented by the ferrierite formed in the second synthesis step. In this way, the crystallinity of the zeolite-based compound may be enhanced. The resulting zeolite-based compound according to the present disclosure has not only the enhanced crystallinity but also, increased Brønsted acid-sites.

The zeolite-based compound according to the present disclosure described above may be used as the catalyst for the production of methyl acetate, that is, as the catalyst for the carbonylation reaction of dimethyl ether, thereby enhancing the selectivity of methyl acetate. In addition, the zeolite-based compound itself has improved catalyst stability.

Specifically, the process of forming dimethyl ether using syngas as a starting material and indirectly synthesizing ethanol and acetic acid may be carried out via following reaction formula 1 to formula 4. In this connection, the following reaction formula 3 (hydrogenation reaction) and the formula 4 (hydration reaction) are subsequent reactions using methyl acetate which is a product of the reaction formula 2 below.

   [Reaction formula 1]

   [Reaction formula 2]

   [Reaction formula 3]

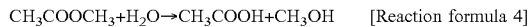   [Reaction formula 4]

That is, dimethyl ether is synthesized by using carbon monoxide and hydrogen via the reaction formula 1. In reaction formula 2, dimethyl ether, which is the product of the reaction formula 1, reacts with carbon monoxide such that carbonylation reaction occurs, to produce methyl acetate. At this time, the zeolite-based compound according to the present disclosure including the zeolite-based core and the H-ferrierite based surface-portion may be used as the catalyst, to enhance the selectivity of the methyl acetate. Therefore, it is possible to enhance the yield of ethanol and/or acetic acid as obtained in the reaction formula 3 and/or the reaction formula 4. In addition, the selectivity of methanol among the by-products which may be generated as a side reaction to the reaction formula 2 may be enhanced, which is advantageous in that the collected methanol may be recycled.

Hereinafter, the present disclosure will be described in more details with reference to specific embodiments and evaluation of catalyst characteristics thereof.

Production of a Present Sample 1 (FER(10)@FER))

(1) Production of FER(10) (Production of a Seed)

After the basic silica solution was stirred for 1 hour, piperidine as the structure-directing agent was added thereto to form a first mixture, which, in turn, was stirred for 10 to 11 hours to form a silica structure. Then, an alumina solution was mixed to the silica structure to form a second mixture which in turn, was stirred at a room temperature for about 12 hours. The resulting second mixture was hydrothermally synthesized. The hydrothermal synthesis was performed as follows: the temperature of the second mixture was raised to 160° C. while the mixture was being stirred, and the mixture was kept at this temperature for 7 days as it is. Then after cooling the mixture to a room temperature, washing and drying processes of the mixture were performed. A resulting compound was fired in an air atmosphere at 550° C. for 6 hours to produce basic-ferrierite.

Then, the basic ferrierite was subjected to sufficient ion exchange with the ammonium precursor. In this connection, per 1 g of the catalyst, 100 mL of 1 M solution of ammonium nitrate was used as the ammonium precursor. At this time, the ion-exchange process was carried out by stirring the basic ferrierite and the ammonium nitrate at 80° C. for 3 hours. Then, the basic ferrierite was subjected to washing and drying processes. Further, a single cycle including a single stirring, washing and drying was repeated six times in total to obtain $NH_3$-ferrierite. Finally, "FER(10)" was produced by firing the obtained $NH_3$-ferrierite at 550° C. for 3 hours to convert the $NH_3$-ferrierite to H-ferrierite (Si/Al atom ratio=10.4 and a specific surface area=333 m²/g).

(2) Synthesis of FER

The substantially same process as the processes of synthesizing the FER(10) was performed, except that the FER (10) as the structure-directing agent was used in place of the piperidine, and hydrothermal synthesis was carried out for 4 days. In this way, H-ferrierite was synthesized on the surface of the FER(10) as produced above. The H-ferrierite synthesized on the surface of the FER(10) is indicated as FER(10) @FER as a present sample 1 according to the present disclosure. In this connection, a content of the FER(10) was 24 parts by weight based on 100 parts by weight of the H-ferrierite synthesized on the surface of the FER(10).

Production of a Present Sample 2 (MOR@FER)

Via substantially the same as the process of producing the present sample 1 except that mordenite (a molar ratio of Si and Al is 8:1) was used as the seed, a present sample 2 (MOR@FER) with the mordenite core and the surface-portion made of the H-ferrierite was produced. In this connection, a content of the mordenite(MOR) was 24 parts by weight based on 100 parts by weight of the H-ferrierite synthesized on the surface of the core.

Production of Present Sample 3 to Present Sample 6

Via substantially the same as the process of producing the present sample 1 except that conventional ferrierite (a molar ratio of Si and Al is 25:1, and the conventional ferrite is indicated as FER(G)) was used as the seed, a present sample 3 (FER(G)@FER) with the conventional core and the surface-portion made of the H-ferrierite was produced. In this connection, a content of the conventional ferrierite (FER (G)) was 24 parts by weight based on 100 parts by weight of the H-ferrierite.

Further, via substantially the same as the process of producing the present sample 1 except that the content of the FER(10) was 19 parts by weight based on 100 parts by weight of the H-ferrierite synthesized on the surface of the core, a present sample 4 (FER(10)@FER-1) was produced.

In addition, via substantially the same as the process of producing the present sample 1 except that a content of the conventional ferrierite (FER(G)) was 14 parts by weight, and 7 parts by weight, respectively based on 100 parts by weight of the H-ferrierite synthesized on the surface of the core, a present sample 5 (FER(10)@FER-2) and a present sample 6 (FER(10)@FER-3) were produced.

Production of a Present Sample 7 and a Present Sample 8

A present sample 7 (ZSM-5@FER) was produced by using a conventional ZSM-5 (Si/A=50) as the seed, via substantially the same process as the processes of producing the present sample 1.

Further, a present sample 8 (YZ@FER) was produced by using a conventional zeolite-Y (ZSM-5@FER) as the seed, via substantially the same process as the processes of producing the present sample 1.

Production of a Comparison Sample 1 to a Comparison Sample 5

FER (10) produced via substantially the same process as the process of the production of the FER(10) in the production of the present sample 1 was designated as a comparison sample 1 (FER(10)). Then, the mordenite is designated as a comparison sample 2, the conventional ZSM-5 as a comparison sample 3. Further, the conventional zeolite-Y as a comparison sample 4, and the conventional ferrierite as a comparison sample 5 (FER(G)) were respectively prepared.

Property Evaluation

Averages of the conversion rate of dimethyl ether and the selectivities of methyl acetate and methanol for each of the present sample 1 to the present sample 8 and the comparison sample 1 to the comparison sample 5 produced as described above.

Before starting the carbonylation reaction of dimethyl ether, the catalyst undergoes a reduction process. The reduction process was performed by raising the temperature to 500° C. under nitrogen gas and keeping the catalyst in the gas for 1 hour. The carbonylation reaction of the dimethyl ether was performed by using gas having the molar ratio (%) of dimethyl ether:carbon monoxide:nitrogen as reactants being 5:45:50 and at 220° C. of a reaction temperature, at 10 kg/cm$^2$ of a reaction pressure, and at 2000 L/kgcat/h of a space velocity. Further, the reaction is carried out for 100 hours with the inflow of the gas in a constant flow rate in order to observe the stability of the catalyst. Consequently, the results were obtained by averaging the conversion rate of the dimethyl ether, the selectivities of the methyl acetate and the methanol based on the time when the reaction was stabilized, that is, based on when the reaction reached the steady state in 30 hours. The results are shown in Table 1 below.

TABLE 1

| Sample | Catalyst | DME conversion rate (mole %) | Carbon selectivity [MA/MeOH/ CH$_4$/by-product] | yield (MA) | yield[1] (MA + MeOH) |
|---|---|---|---|---|---|
| Comparison sample 1 | FER(10) | 16.3 | 97.0/1.5/1.3/0.2 | 13.1 | 13.3 |
| Present sample 1 | FER(10)@ FER | 39.9 | 98.5/0.5/0.9/0.1 | 32.6 | 32.7 |
| Present sample 2 | MOR@ FER | 28.3 | 98.2/0.4/1.2/0.2 | 23.0 | 23.1 |
| Present sample 3 | FER(G)@ FER | 27.4 | 96.9/1.8/1.2/0.1 | 22.0 | 22.4 |
| Present sample 4 | FER(10) FER-1 | 34.8 | 99.2/0.1/0.6/0.1 | 34.5 | 34.6 |
| Present samples 5 | FER(10)@ FER-2 | 38.8 | 99.1/0.1/0.7/0.1 | 38.5 | 38.5 |
| Present sample 6 | FER(10)@ FER-3 | 40.5 | 98.6/0.3/1.0/0.1 | 39.9 | 40.1 |
| Comparison sample 2 | MOR | 3.6 | 35.1/20.4/5.5/39.0 | 1.1 | 1.7 |
| Comparison sample 3 | ZSM-5 | 4.4 | 12.4/34.3/3.6/49.7 | 0.5 | 1.7 |
| Comparison sample 4 | YZ | 12.9 | 37.1/32.7/3.8/26.4 | 4.0 | 7.5 |
| Comparison samples | FER(G) | 18.9 | 93.9/4.1/1.9/0.1 | 14.7 | 15.3 |
| Present sample 7 | ZSM5@ FER | 15.3 | 92.1/5.4/1.7/0.8 | 11.7 | 12.4 |
| Present sample 8 | YZ@ FER | 13.4 | 96.1/1.8/1.8/0.3 | 10.6 | 10.8 | yield[1]: Yield of mixture of methyl acetate as the main product, and methanol, which may be used in the recycling process, DME: dimethyl ether, MA: methyl acetate, MeOH: methanol Referring to Table 1, it may be confirmed that using the present samples 1 to the present sample 6 as the catalyst indicates the remarkably high DME conversion rate as compared with the comparison sample 1 to the comparison sample 5. In particular, it may be confirmed that the present sample 1 and the present sample 4 to the present sample 6 exhibited the high selectivity of MA as a product, and the remarkably high DME conversion rate.

It may also be confirmed that the present sample 2 and the present sample 3 exhibited the higher DME conversion rate and MA selectivity than the comparison sample 1 to the comparison sample 5. It may be confirmed that using the present sample 7 or the present sample 8 as the catalyst indicates that the DME conversion rate was similar to that of the comparison samples 1, 4 and 5, but the MA selectivity was quite higher than that of comparison samples.

It may be confirmed from comparing the comparison sample 5 with the present sample 3, that the present sample 3 according to the present disclosure exhibit the DME conversion rate increase by about 20% and the MA selectivity increase as compared with the comparison sample 5. Thus, the present sample 3 is excellently activated in the DME carbonylation. Further, it may be confirmed that the present sample 2 using the mordenite as the seed shows significantly reduced inactivation compared with the comparison example 2 using only the mordenite without the surface portion made of H-ferrierite. These results indicate that the defect points of a mordenite phase may be complemented for by the ferrierite formed on the surface of the mordenite core and may simultaneously induce crystallization thereof. Thus, this may lead to excellent activation in the DME carbonylation reaction.

In addition, when the zeolite itself is used as in the comparison sample 3 or the comparison sample 4, hydrocarbons are predominantly produced as a by-product. To the contrary, when the zeolite produced as in the present sample 7 or the present sample 8 is used as the catalyst, the zeolite shows high activation. However, it may be confirmed that, for the present sample 7 or the present sample 8, the DME conversion rate is relatively low. Therefore, it may be confirmed that the present sample 1 to the present sample 6, particularly using ferrierite or mordenite as the seed, among the present sample 1 to the present sample 8, may secure the excellent MA yield.

Structural Analysis-1: XRD Analysis

X-ray diffraction (XRD) analysis was performed on each of the prepared present samples 1, 2, 3, 7 and 8 and the comparison sample 1. In addition, an acid-site analysis was performed for each sample. The results are shown in FIG. 1 and Table 2 below.

TABLE 2

| Sample | XRD (%) crystallinity[1] | $NH_3$-TPD (acid-sites, mmol $NH_3$/g) | | |
|---|---|---|---|---|
| | | weak acid-sites | strong acid-sites | total acid-sites |
| Comparison sample 1 FER(10) | 93.5 | 0.74 | 0.48 | 1.22 |
| Present sample 1 FER(10) @ FER | 100 | 0.94 | 0.85 | 1.79 |
| Present sample 2 MOR @ FER | 85.4 | 0.65 | 0.46 | 1.11 |
| Present sample 3 FER(G) @ FER | 86.1 | 0.94 | 0.52 | 1.46 |
| Present sample 7 ZSM5 @ FER | 76.8 | 0.93 | 0.30 | 1.23 |
| Present sample 8 YZ @ FER | 80.3 | 0.95 | 0.27 | 1.22 | crystallinity[1]: The crystallinity of the present sample 1 was set to 100 and the relative crystallinities of other zeolites were shown, and the acid-site was measured using a $NH_3$-TPD method.

FIG. 1 shows the XRD analysis result of the H-ferrierite and the present samples according to the present disclosure.

Referring to FIG. 1 and Table 2, it may be confirmed that the crystallinity of the comparison sample 1 is lower than that of the present sample 1. That is, when the surface-portion formed on the zeolite-based seed is used as in the present disclosure, the crystallinity is higher than when the seed only is used. In other words, the comparison sample 1 itself may not have perfect crystallinity but crystal defects. To the contrary in the case of the present sample 1, the crystallinity is complemented and is enhanced. This high crystallinity has the same tendency as that of the increase of the activation.

Meanwhile, it may be confirmed that when the present samples 1 to 3, 7 and 8 are compared with each other, the crystallinity of the present sample 1 is the best.

Further, it was confirmed from a result of the acid-site analysis using the $NH_3$-TPD method, that re-synthesis of the sample using the FER seed results in the Brønsted acid-site increase.

Structural Analysis-2: SEM Analysis

FIG. 2 shows the SEM images of the H-ferrierite and the present samples according to the present disclosure. FIG. 3 shows the SEM images of the comparison samples.

When FIG. 2 and FIG. 3 are compared with each other, it may be confirmed that the surface-portion in the form of the plate is coated on the surface of the zeolite-based core as a seed. That is, it may be confirmed from this that the surface-portion is formed with synthesis from the seed.

It will be understood that while the foregoing disclosure has been described with reference to the preferred embodiments of the present disclosure, those skilled in the art are may alter and modify the present disclosure without departing from the spirit and scope of the present disclosure as defined in the following claims.

What is claimed is:

1. A zeolite-based composition having a high crystallinity, the composition comprising:
   a zeolite-based core; and
   a ferrierite surface-portion formed on at least a portion of a surface of the zeolite-based core, wherein the ferrierite surface-portion has a molar ratio of silicon and aluminum in a range of 5:1 to 30:1.

2. The zeolite-based composition according to claim 1, wherein the ferrierite constituting the surface-portion is coated in a form of a plate on the surface of the zeolite-based core.

3. The zeolite-based composition according to claim 1, wherein the zeolite-based core comprises at least one selected from a group consisting of H-ferrierite, mordenite, ZSM-5, and zeolite-Y.

4. A zeolite-based composition comprising:
   zeolite-based core; and
   a ferrierite surface-portion formed on at least a portion of a surface of the zeolite-based core,
   wherein the zeolite-based core is made of a zeolite-based material including silicon and aluminum, wherein a molar ratio of the silicon and aluminum is in a range of 10:1 to 11:1.

5. The zeolite-based composition according to claim 1, wherein the zeolite-based core and the surface-portion together form a core/shell structure.

6. A method for producing a zeolite-based composition having a high crystallinity, the method comprising:
   synthesizing a seed made of a zeolite-based material; and
   synthesizing ferrierite on a surface of the seed using the seed as a structure-directing agent,
   wherein the seed defines a zeolite-based core of the zeolite-based composition, wherein the ferrierite is formed on at least a portion of the surface of the zeolite-based core, wherein the ferrierite defines a ferrierite surface-portion of the zeolite-based composition, and
   wherein the ferrierite surface-portion has a molar ratio of silicon and aluminum in a range of 5:1 to 30:1.

7. The method of claim 6, wherein in synthesizing the ferrierite on the surface of the seed, the ferrierite formed on the surface of the seed compensates for crystal defects of the seed to enhance an overall crystallinity of the composition.

8. The method of claim 6, wherein synthesizing the ferrierite on the surface of the seed includes:
   producing a silica structure using a basic silica solution and the seed as a structure-directing agent;
   hydrothermally synthesizing the silica structure with an alumina solution to form a hydrothermally synthesized product;
   firing the hydrothermally synthesized product to produce a basic-ferrierite;
   ion-exchanging the basic-ferrierite with an ammonium precursor to produce $NH_3$-ferrierite; and
   firing the $NH_3$-ferrierite to form the H-ferrierite on the surface of the seed.

9. The method of claim 8, wherein synthesizing the seed comprises:
   producing a silica structure using a basic silica solution and piperidine as a structure-directing agent;

hydrothermally synthesizing the silica structure with an alumina solution to form a hydrothermally synthesized product;

firing the hydrothermally synthesized product to produce a basic-ferrierite;

ion-exchanging the basic-ferrierite with an ammonium precursor to produce $NH_3$-ferrierite; and firing the $NH_3$-ferrierite to form H-ferrierite as the seed.

10. A method for producing methyl acetate comprising:

performing carbonylation of dimethyl ether using a catalyst, wherein the catalyst is a zeolite-based composition having a high crystallinity, wherein the composition includes a zeolite-based core, and a ferrierite surface-portion formed on at least a portion of a surface of the zeolite-based core, wherein the ferrierite surface-portion has a molar ratio of silicon and aluminum in a range of 5:1 to 30:1.

11. The zeolite-based composition according to claim 1, wherein an overall crystallinity of the zeolite-based core and the surface-portion formed thereon is higher than a crystallinity of the zeolite-based core alone.

12. The zeolite-based composition according to claim 1, wherein the composition has a ratio in a range of 7-24 parts by weight of the zeolite-based core to 100 parts by weight of the surface-portion.

* * * * *